United States Patent [19]

Saville

[11] Plant 4,699

[45] Apr. 28, 1981

[54] ROSE PLANT

[75] Inventor: F. Harmon Saville, Rowley, Mass.

[73] Assignee: F. Harmon Saville, Nor'East Miniature Roses, Inc., Rowley, Mass.

[21] Appl. No.: 125,511

[22] Filed: Feb. 28, 1980

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

The new orange toned miniature rose which lightens to orange buff and Spanish orange tonality upon aging.

1 Drawing Figure

The present invention relates to a new and distinct variety of rose plant of the miniature rose class, which was originated by my crossing as seed parent the rose known as "Rise 'N Shine" and the rose known as "Sheri Anne" as pollen parent.

Among the novel characteristics possessed by this new variety which distinguish it from its parents and all other varieties of which I am aware are flowers of unusual and varying orange tones borne singly and in sprays and which lighten differently upon aging to orange buff, Spanish orange or peach colors. Asexual reproduction by budding of the new variety as performed in Essex County, Mass., shows that the foregoing and other distinguishing characteristics come true to form and are established and transmitted through succeeding propagations.

The new and improved rose variety which I have developed is an unusual miniature rose in its coloring. An attractive feature of this variety is that flowers of varying orange tone are often visible at the same time. Plants of the new variety flower profusely and are colorfully eye catching. This variety propagates readily from cuttings and is especially well suited for pot-forcing.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "33B" is plate 33B of the Royal Horticultural Society Color Chart.

Parentage: Seedling.

*Seed parent.*—"Rise 'N Shine".

*Pollen parent.*—"Sheri Anne".

Class: Miniature.

The following observations are made of specimens grown in a greenhouse in Essex County, Mass., during the month of April.

1. FLOWER

Blooming habit: Profuse, near continuous.

A. Bud:

(1) *Size.*—Medium.

(2) *Form.*—Ovate, pointed.

(3) *Color.*—When sepals first divide and petals begin to unfurl—color is variously 32B, 33B and 34C.

(4) *Sepals.*—Foliated, long, thin; one sepal may be slightly foliated.

(5) *Peduncle.*—Length—medium. Aspect—straight. Strength—erect, firm. Color—near to 144A.

B. Bloom:

(1) *Size.*—Average size when fully expanded—about $1\frac{1}{4}$ inches.

(2) *Borne.*—Singly and in sprays.

(3) *Form.*—Relatively high centered at first, becoming flat upon opening.

(4) *Petalage.*—Number of petals under normal conditions—about 35 to 40.

(5) *Color.*—As the relatively darker-colored orange red bud opens, the flowers appear more uniformly colored to the half-open stage which may be described as Spanish orange 26C or of a tonality between 25C and 26C sometimes approaching marigold orange 28C. Upon further opening and aging the flower color becomes, variously orange buff 22C or peach colored 29D to 29C.

C. Petals:

(1) *Texture.*—Medium.

(2) *Appearance.*—Inside—satiny: Outside—satiny.

(3) *Form.*—Quilling to a star-like point by folding under.

(4) *Arrangement.*—Regularly arranged, shingle-like.

(5) *Petaloids in center.*—Medium.

(6) *Persistence.*—Slow to drop but drop off cleanly.

(7) *Fragrance.*—Slight.

(8) *Lasting quality.*—Long lasting on plant and as cut flower.

2. REPRODUCTIVE ORGANS

A. Stamens, filaments and anthers:

(1) *Arrangement.*—Stamens regularly arranged around styles.

(2) *Color.*—21C.

B. Pollen: Color—21B.

C. Styles: Even, medium length.

D. Stigmas: Color—4D.

E. Hips: Globular, $\frac{3}{8}$ to $\frac{1}{2}$-inch diameter, orange red color, seeds do not usually protrude.

3. PLANT

A. Form: Upright, compact, well rounded outlining.

B. Growth: Vigorous, free branching. Height attained—12 to 14-inches.

C. Foliage: Compound 5 to 7 leaflet leaves.

(1) *Size.*—Medium.

(2) *Quantity.*—Abundant, well spaced.

(3) *Color.*—New foliage—upper side 137B; under side 138B. Old foliage—upper side 137A. under side 138B.

(4) *Shape.*—Pointed, oval, long.

(5) *Texture.*—Upper side—slightly glossy. Under side—matte.

(6) *Edge.*—Serrated.

(7) *Serration.*—Numerous, pronounced serrations.

(8) *Leaf stem.*—Color—near to 139C. Under Side—near to 146D.

(9) *Stipules.*—Medium length, slightly bearded, long thin point.

(10) *Resistance to disease.*—Blackspot—average. Mildew—average.

D. Wood:

(1) *New wood.*—Color—near 146C. Bark—smooth.

(2) *Old wood.*—Color—near to 148A. Bark—smooth.

E. Thorns:

(1) *Thorns.*—Quantity—ordinary. On laterals from stalk—ordinary. Form—long, thin, needle point. Length—long. Color (when young)—51D at base lightening toward point. Position—irregular.

(2) *Prickles.*—Few.

F. Winter hardiness: Needs ordinary protection in extreme climate.

I claim:

1. A new and distinct variety of rose plant of the miniature class, substantially as shown and described, characterized particularly by orange tone blooms borne singly and in sprays on a vigorous plant which alter to orange buff, Spanish orange and peach coloring upon aging.

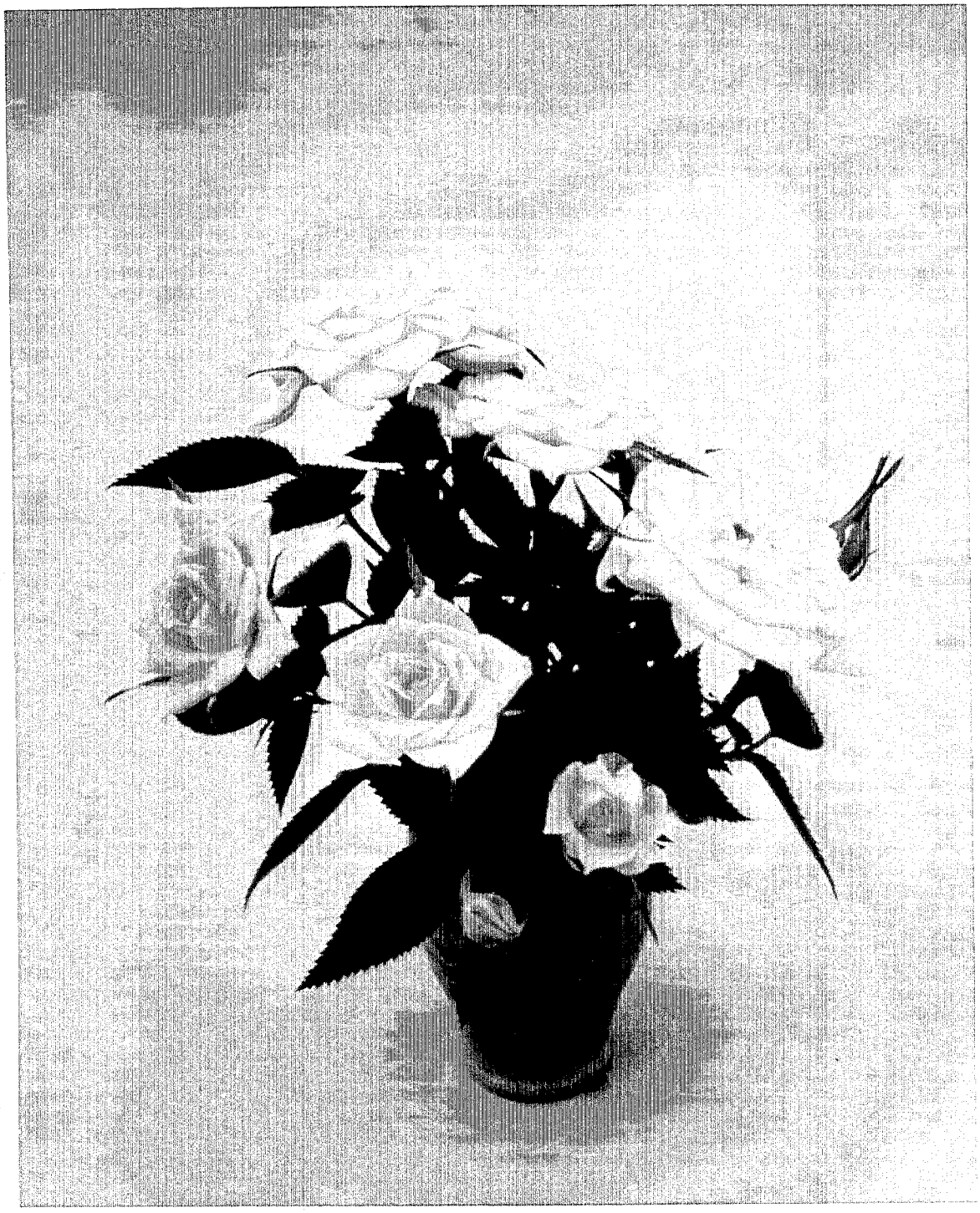

* * * * *